(12) United States Patent
Georgeson et al.

(10) Patent No.: US 9,310,317 B2
(45) Date of Patent: Apr. 12, 2016

(54) AUTOMATED SYSTEM AND METHOD FOR TRACKING AND DETECTING DISCREPANCIES ON A TARGET OBJECT

(75) Inventors: Gary E. Georgeson, Tacoma, WA (US); James J. Troy, Issaquah, WA (US); Scott W. Lea, Renton, WA (US)

(73) Assignee: The Boeing Company, Chicago, IL (US)

( * ) Notice: Subject to any disclaimer, the term of this patent is extended or adjusted under 35 U.S.C. 154(b) by 465 days.

(21) Appl. No.: 13/357,768

(22) Filed: Jan. 25, 2012

(65) Prior Publication Data

US 2013/0188059 A1 Jul. 25, 2013

(51) Int. Cl.
    H04N 5/225    (2006.01)
    G01N 21/95    (2006.01)
    G01N 21/94    (2006.01)
    G01S 17/87    (2006.01)
    G01N 21/952   (2006.01)
    G01B 11/24    (2006.01)

(52) U.S. Cl.
    CPC ............ *G01N 21/9515* (2013.01); *G01B 11/24* (2013.01); *G01N 21/94* (2013.01); *G01N 21/952* (2013.01); *G01S 17/875* (2013.01)

(58) Field of Classification Search
    None
    See application file for complete search history.

(56) References Cited

U.S. PATENT DOCUMENTS

| | | | |
|---|---|---|---|
| 4,895,448 A | 1/1990 | Laird | |
| 6,064,429 A | 5/2000 | Belk et al. | |
| 6,809,728 B2 * | 10/2004 | Terauchi | G06T 1/0007 345/420 |
| 7,236,625 B2 | 6/2007 | Engelbart et al. | |
| 7,307,001 B2 | 12/2007 | Lin et al. | |
| 7,480,037 B2 | 1/2009 | Palmateer et al. | |
| 7,495,758 B2 | 2/2009 | Walton | |
| 7,576,850 B2 | 8/2009 | Engelbart et al. | |
| 7,678,214 B2 | 3/2010 | Engelbart et al. | |
| 7,688,434 B2 | 3/2010 | Engelbart et al. | |
| 7,712,502 B2 | 5/2010 | Engelbart et al. | |
| 7,835,567 B2 | 11/2010 | Oldani | |
| 7,859,655 B2 | 12/2010 | Troy et al. | |

(Continued)

FOREIGN PATENT DOCUMENTS

| | | |
|---|---|---|
| CN | 1822314 A | 8/2006 |
| CN | 101784804 A | 7/2010 |

(Continued)

OTHER PUBLICATIONS

State Intellectual Property Office of PRC, First Official Action, Chinese Pat. App. No. 201280067976X (Dec. 21, 2015).

*Primary Examiner* — Christopher S Kelley
*Assistant Examiner* — Kaitlin A Retallick
(74) *Attorney, Agent, or Firm* — Walters & Wasylyna LLC

(57) ABSTRACT

A detection system including a target object having a target object coordinate system, a tracking unit configured to monitor a position and/or an orientation of the target object and generate a target object position signal indicative of the position and/or the orientation of the target object, a camera positioned to capture an image of the target object, an orienting mechanism connected to the camera to control an orientation of the camera relative to the target object, and a processor configured to analyze the image to detect a discrepancy in the image and, when the discrepancy is present in the image, determine a location of the discrepancy relative to the target object coordinate system based at least upon the target object position signal and the orientation of the camera, and then orient the camera and laser to aim at and point out the discrepancy.

20 Claims, 3 Drawing Sheets

(56) References Cited

U.S. PATENT DOCUMENTS

| | | |
|---|---|---|
| 8,044,991 B2 | 10/2011 | Lea et al. |
| 8,050,486 B2 | 11/2011 | Walton |
| 8,539,811 B2 | 9/2013 | Wilhelmy et al. |
| 2004/0206891 A1* | 10/2004 | Ma ................... G01N 21/21 250/225 |
| 2005/0205781 A1* | 9/2005 | Kimba ........ G01N 21/95607 250/311 |
| 2006/0108048 A1 | 5/2006 | Engelbart et al. |
| 2006/0109454 A1 | 5/2006 | Engelbart et al. |
| 2006/0148109 A1* | 7/2006 | Lin ................. G03F 7/70383 438/4 |
| 2007/0263229 A1 | 11/2007 | March |
| 2007/0280501 A1 | 12/2007 | Walton |
| 2008/0163140 A1* | 7/2008 | Fouquet ............... G03F 1/84 700/110 |
| 2008/0289742 A1 | 11/2008 | Engelbart et al. |
| 2009/0086014 A1* | 4/2009 | Lea ..................... G01C 11/00 348/25 |
| 2010/0085437 A1* | 4/2010 | Troy ..................... G01S 5/163 348/211.7 |
| 2010/0153051 A1 | 6/2010 | Georgeson et al. |
| 2010/0180664 A1* | 7/2010 | Wilhelmy ............ F16C 19/52 73/7 |
| 2010/0204929 A1 | 8/2010 | Engelbart et al. |
| 2011/0074952 A1* | 3/2011 | Reidel .................... G06K 9/03 348/143 |
| 2011/0137615 A1 | 6/2011 | Motzer et al. |
| 2011/0149266 A1 | 6/2011 | Motzer et al. |
| 2011/0295427 A1 | 12/2011 | Motzer et al. |

FOREIGN PATENT DOCUMENTS

| | | |
|---|---|---|
| WO | 03/032129 | 4/2003 |
| WO | 2011/138741 | 11/2011 |

* cited by examiner

AUTOMATED SYSTEM AND METHOD FOR TRACKING AND DETECTING DISCREPANCIES ON A TARGET OBJECT

FIELD

The present disclosure generally relates to detection systems and, more particularly, to systems and methods for locating and detecting discrepancies on a target object even when the target object has moved.

BACKGROUND

Discrepancies, such as foreign object debris, can present an expensive and challenging issue during the repair or manufacture of composite structures (e.g., aircraft skin). Failure to detect and remove a discrepancy can result in a decrease in the structural integrity of the composite structures. Furthermore, if discrepancies are not detected early enough in the composite structure manufacturing process, the resulting composite structures may be disposed, repaired or, in some cases, approved through engineering analysis and qualification. Each option can be costly.

Furthermore, some discrepancies may be minute in size or near a bond line, which can result in a detection failure. Failure to timely detect these discrepancies may result in significant damage to the structure, which may be costly to repair. As such, there exists a need to detect and remove the discrepancies as soon as they become attached to the composite structures.

Current methods of discrepancy detection include human or visual based detection systems, which are frequently subject to error. Computerized detection systems have been employed to detect discrepancies via acoustic, laser-based, magnetic, RFID, GPS, and motion capture-based systems. However, such systems typically only work on a stationary target object, and cannot successfully point out discrepancies on moving objects, such as a rotating aircraft fuselage during the manufacture process.

Accordingly, there exists a need for a local positioning-based system that is capable of tracking a target object, determining the positions of discrepancies on the target object, and accurately indicating those discrepancies at a later time, even when the target object has moved.

SUMMARY

In one embodiment, the disclosed detection system may include a target object having a target object coordinate system, a tracking unit configured to monitor a position and/or an orientation of the target object and generate a target object position signal indicative of the position and/or the orientation of the target object, a camera positioned to capture an image of the target object, an orienting mechanism connected to the camera to control an orientation of the camera relative to the target object, and a processor configured to analyze the image to detect a discrepancy in the image and, when the discrepancy is present in the image, determine a location of the discrepancy relative to the target object coordinate system based at least upon the target object position signal, the orientation of the camera, and the location of the discrepancy in the image.

In another embodiment, the disclosed detection system may include a target object having a target object coordinate system, a motion actuator coupled to the target object to control a position and/or an orientation of the target object, a tracking unit configured to monitor the position and/or the orientation of the target object and generate a target object position signal indicative of the position and/or the orientation of the target object, a local positioning system ("LPS") instrument positioned relative to the target object, the LPS instrument including a camera configured to capture an image of the target object, a laser emitting device configured to project a laser beam onto the target object and an orienting mechanism connected to the camera and the laser emitting device to control an orientation of the camera and an orientation of the laser emitting device, and a processor configured to analyze the image to detect a discrepancy in the image and, when the discrepancy is present in the image, determine a location of the discrepancy relative to the target object coordinate system based at least upon the target object position signal and the orientation of the camera, wherein the processor is further configured to project the laser beam onto the discrepancy by controlling the orientation of the laser emitting device based on the location of the discrepancy relative to the target object coordinate system.

In yet another embodiment, disclosed is a method for detecting a discrepancy on a target object having a target object coordinate system. The method may include the steps of (1) providing a local positioning system instrument including a camera, a laser emitting device and an orienting mechanism for orienting the camera and the laser emitting device relative to the target object, (2) providing a motion actuator configured to selectively move the target object, (3) providing a tracking unit configured to monitor at least one of a position and an orientation of the target object, (4) determining an initial position of the local positioning system instrument relative to the target object, (5) moving the target object to a first target object position or orientation, (6) orienting the camera relative to the target object to a first camera orientation, (7) capturing an image of a region on a surface of the target object when the target object is in the first target object position and the camera is in the first camera orientation, (8) comparing the captured image to the corresponding reference image to determine whether the discrepancy is present in the captured image, (9) when the discrepancy is present in the image, determining coordinates of the discrepancy in the target object coordinate system, and (10) moving the laser to point at the discrepancy.

Other aspects of the disclosed automated detection system and method will become apparent from the following detailed description, the accompanying drawings and the appended claims.

DETAILED DESCRIPTION

Figure 1:
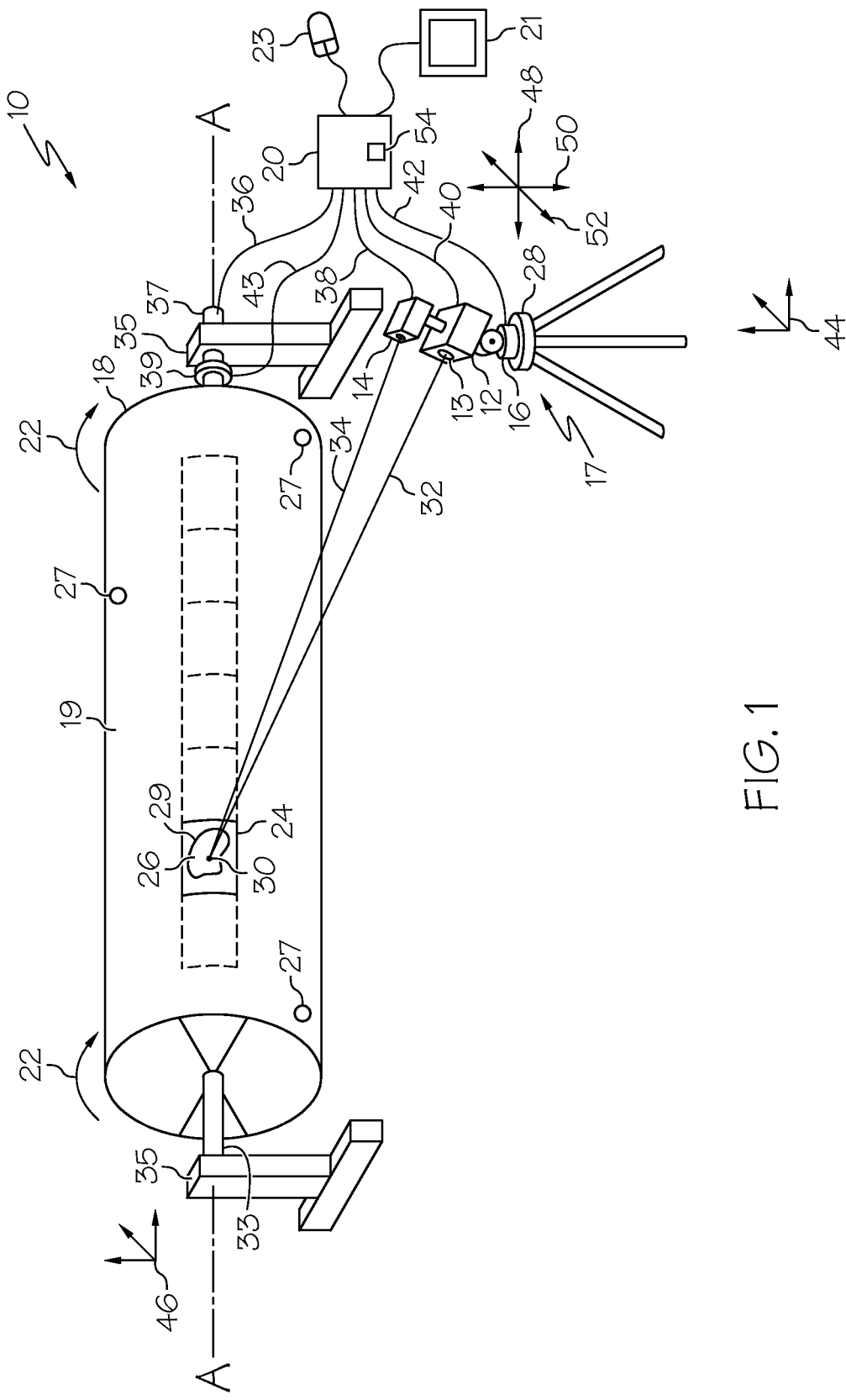
FIG. 1 is a schematic perspective view of one embodiment of the disclosed detection system.

Referring to FIG. 1, one embodiment of the disclosed local positioning-based automated detection system, generally designated 10, may include a processor 20, a memory 54, a tracking unit 37, a controllable motion actuator 39, a camera 12 and a laser emitting device 14. The disclosed local positioning-based automated detection system 10 may further include a support 28 for supporting the camera 12 and an orienting mechanism 16 for orienting the camera 12 and the laser emitting device 14 relative to a target object 18.

Thus, the camera 12, the laser emitting device 14, the orienting mechanism 16 and the support 28 may comprise a local positioning system instrument 17 of the disclosed local positioning-based automated detection system 10. The local positioning system instrument 17 may have a coordinate system 44.

The laser emitting device 14 may be capable of emitting a laser beam and functioning as a laser range meter for determining the distance between the local positioning system instrument 17 and the target object 18. Alternatively, a separate laser range meter may be included as part of the location positioning system instrument 17. Those skilled in the art will appreciate that use of a laser range meter capable of determining the distance between the local positioning system instrument 17 and the target object 18 may aid in the calibration process discussed below.

The disclosed local positioning-based automated detection system 10 may be employed to (1) track the position and/or orientation of the target object 18, (2) detect a discrepancy 26 on a surface 19 on the target object 18, (3) determine the location of the discrepancy 26 relative to the coordinate system 46 of the target object 18, and (4) provide a visual indication (e.g., laser point) of the discrepancy 26 on the target object 18.

As used herein, "discrepancy" refers to any type of inconsistency, difference or irregularity that is not an intended component or feature of the target object 18. Examples of "discrepancies" include, but are not limited to, foreign object debris (e.g., dust, scrap), damaged areas (e.g., blemishes, dents), mislaid or malformed components (e.g., mislaid plies), missing components (e.g., missing plies) and the like.

Thus, a discrepancy 26 may be defined by one or more points of interest 30 on the target object 18, and may define a discrepancy boundary 29.

The processor 20 may be configured to receive data from the camera 12 and, based on the received data, locate a discrepancy 26 on the target object 18. The processor 20 may be also be configured to determine the location of the discrepancy 26 relative to the coordinate system 46 of the target object 18 based at least upon the position of the camera 12 relative to the target object 18, the position/orientation of the target object 18, and the orientation of the camera 12. The processor 20 may generate a command signal to control the laser emitting device 14 such that the laser emitting device 14 may provide a visual indication of the location of the discrepancy 26 on the target object 18.

The processor 20 may communicate with the laser emitting device 14 by way of a processor-laser pathway 38. Communication between the processor 20 and the laser emitting device 14 may be one-way communication (e.g., from the processor 20 to the laser emitting device 14) or two-way communication (e.g., from the processor 20 to the laser emitting device 14 and from the laser emitting device 14 to the processor 20).

The processor 20 may communicate with the camera 12 by way of a processor-camera pathway 40. Communication between the processor 20 and the camera 12 may be one-way communication (e.g., from the camera 12 to the processor 20) or two-way communication (e.g., from the processor 20 to the camera 12 and from the camera 12 to the processor 20).

The processor 20 may communicate with the orienting mechanism 16 by way of a processor-mechanism pathway 42. Communication between the processor 20 and the orienting mechanism 16 may be one-way communication (e.g., from the processor 20 to the orienting mechanism 16) or two-way communication (e.g., from the processor 20 to the orienting mechanism 16 and from the orienting mechanism 16 to the processor 20).

The processor 20 may communicate with the tracking unit 37 by way of a processor-tracker pathway 36. Communication between the processor 20 and the tracking unit 37 may be a one-way communication (e.g., from the tracking unit 37 to the processor 20).

The processor 20 may communicate with the controllable motion actuator 39 by way of a processor-actuator pathway 43 to translate or rotate the target object 18. Communication between the processor 20 and the motion actuator 39 may be one-way communication (e.g., from the processor 20 to the motion actuator 39) or two-way communication (e.g., from the processor 20 to the motion actuator 39 and from the motion actuator 39 to the processor 20).

The processor-laser pathway 38, the processor-camera pathway 40, the processor-mechanism pathway 42, the processor-tracker pathway 36 and the processor-actuator pathway 43 may include any mode of transmitting data. As one example, the pathways 36, 38, 40, 42, 43 may be wired pathways, such as electrical cables, optical cables and the like. As another example, the pathways 36, 38, 40, 42, 43 may be wireless pathways, such as Bluetooth, near-field communication, infrared communication and the like.

The processor 20 may be any type of computational or processing device capable of executing programming instructions, codes, binary programming and the like. The processor 20 may further be a controller, microprocessor, microcontroller, or state machine, and may be or may include a signal processor, digital processor, embedded processor, microprocessor or any variant such as a co-processor (e.g., mathematical co-processor, graphical processing unit (GPU), communications co-processor) and the like that may directly or indirectly facilitate execution of program code or program instructions stored thereon. The processor 20 may further contain multiple processing cores, or be a collection of processing units configured to form a distributed processing system. In addition, the processor 20 may enable execution of multiple programs, threads, and codes.

The processor 20 may further be encompassed within an electronic device, including, but not limited to personal computers, tablet computers, smartphones, and the like. The processor 20 may alternatively be encompassed within one of the other components described in the present disclosure, including the camera 12 and the laser emitting device 14.

The processor 20 may include image processing functionality. The image processing functionality may be image processing software or hardware, and may be configured to receive an image (or a series of images) from the camera 12 and analyze the image to detect and locate discrepancies 26. During image processing, the images received from the camera 12 may be compared to a reference image, which may be a single image, a series of images or a mosaic of images. The comparison process may enable the processor 20 to detect discrepancies 26 on the target object 18 within the camera's field of view 24.

The reference image may be an image that has been stored to the memory 54 from a database of known three dimensional models that typically embody the target object 18, may be an image previously obtained by the camera 12 and stored in the memory 54, or may be an image that has been obtained by other means and stored to the memory 54.

The processor 20 may include memory 54 for storing data, such as reference images, coordinates, methods, codes, instructions and programs. The processor 20 may access the memory 54 through an interface. The memory 54 may be any electronic storage device including, but not limited to, one or more of a CD-ROM, DVD, Blu-ray, memory, hard disk, flash drive, RAM, ROM, cache, and any combination thereof.

The tracking unit 37 may be any apparatus or system capable of sensing or otherwise monitoring the position and/or the orientation of the target object 18. For example, the tracking unit 37 may be a position encoder, such as a rotary encoder, and may track the rotational position/orientation of the target object 18 relative to the support structure 35. The data collected by the tracking unit 37 may be communicated to the processor 20 by way of the processor-tracker pathway 36.

For example, the target object 18 may not be stationary, but rather may be attached to a shaft 33 connected to a support structure 35 such that the target object 18 rotates about an axis A, as shown by arrow 22. The tracking unit 37 may track the rotational position and/or orientation of the target object 18, and may communicate position/orientation data to the processor 20 by way of the processor-tracker pathway 36.

At this point, those skilled in the art will appreciate that the target object 18 may grow during processing, such as when additional layers (e.g., plies) are applied to the target object 18. Such growth of the target object 18 may reduce the distance between the target object 18 and the local positioning system instrument 17. However, the laser range meter functionality of the laser emitting device 14 may detect such growth and may recalibrate the system accordingly.

The controllable motion actuator 39 may be any apparatus or system capable of effecting movement, such as translation or rotation, of the target object 18. Examples of suitable controllable motion actuators 39 include, but are not limited to, motors (e.g., electric motors), hydraulic pumps, air cylinders, linear actuators and the like.

In one construction, the controllable motion actuator 39 may be coupled to the shaft 33 to selectively rotate the target object 18 about the axis A. The controllable motion actuator 39 may be coupled to the shaft 33 by, for example, a belt, a pulley or a screw. In another construction, the controllable motion actuator 39 may be connected directly to the target object 18 to selectively rotate the target object 18 about the axis A.

Thus, when the shape of the target object 18 is known, such as when the processor 20 is provided with a three-dimensional model of the target object 18, the initial position and orientation of the local positioning system instrument 17 may be determined. Then, with the initial position and orientation of the local positioning system instrument 17 known, the position/orientation data received from the tracking unit 37, as well as the position/orientation data received from the orientation mechanism 16, may allow the processor 20 to determine the location of discrepancies 26 relative to the coordinate system 46 of the target object 18.

Based on the position/orientation data received from the tracking unit 37, the processor 20 may determine whether it is necessary to reposition the target object 18. If repositioning is necessary, the processor 20 may send control signals to the controllable motion actuator 39 by way of pathway 43. The controllable motion actuator 39 may receive the signals from the processor 20, and based upon those signals, may reposition (e.g., rotate) the target object 18 relative to the support structure 35.

The camera 12 may be any device having a field of view 24 (i.e., the visible horizontal and vertical extents of an image received by the camera 12) and being capable of collecting images of the target object 18 within the field of view 24. For example, the camera 12 may be a digital single lens reflex (SLR) camera, a stop-motion camera, a video camera for taking moving video images, a three-dimensional (3D) camera, a digital camera, a film camera, a web camera, a stereo camera or the like, or any combinations thereof.

The camera 12 may include a lens 13, and may generally be part of a system particularly adapted to view the surface 19 of the target object 18. The camera 12 may further contain any type of recording mechanism, as well as a storage medium such as a memory or the like for storing images that have been captured. The camera 12 may also contain a means for controlling the field of view 24 and range, such as the field of view angle controlled by the zoom functionality.

Optionally, the field of view 24 of the camera 12 may be viewed on any suitable viewing device 21 (e.g., a monitor, a projector or the like) coupled to the processor 20.

The camera 12 may be supported on the support 28. The local positioning system instrument 17 may be positioned a distance from the target object 18 such that the camera 12 may view (or may be oriented to view) a region of interest on the target object 18. For example, the local positioning system instrument 17 may be positioned about 40 feet from the target object 18. At this point, those skilled in the art will appreciate that the actual distance of the local positioning system instrument 17 from the target object 18 may be precisely determined during calibration.

The orienting mechanism 16 may adjust the orientation of the camera 12 with respect to the target object 18, thereby moving the field of view 24 relative to the target object 18. The orienting mechanism 16 may be manually adjusted or fully automated (e.g., driven by a number of servos or other similar devices).

In one implementation, the orienting mechanism 16 may facilitate movement of the camera 12 along one axis. For example, the orienting mechanism 16 may be a uni-track system, a slider video system or the like, and may allow the camera 12 to reciprocate along an axis that is parallel with (but spaced from) the rotational axis A of the target object 18.

In another implementation, the orienting mechanism 16 may be a pan-tilt mechanism. The pan-tilt mechanism may be capable of positionally adjusting the camera 12 to selected angles around the vertical, azimuth (pan) axis 50 and the horizontal, elevation (tilt) axis 52. Orienting mechanisms that facilitate motion along other axes, such as a roll axis, are also contemplated.

A direction vector that describes the orientation of the camera 12 relative to the coordinate system 44 associated with the local positioning system instrument 17 may be determined from the azimuth and elevation angles, as well as the center of a crosshair marker (not shown) that may be present in the field of view 24 of the camera 12 when it is aimed at a point of interest 30, such as the location of a discrepancy 26 on the surface 19 of the target object 18. The location of the crosshair marker may be at any location, and may not necessarily be at the center of the field of view 24 of the camera 12. This direction vector may be thought of as a line 32 extending from the lens 13 of the camera 12 and intersecting at a location 30 on the surface 19 of the target object 18.

The operation of the camera 12 and the movement of the camera 12 by the orienting mechanism 16 (e.g., scanning the field of view 24 across the target object 18) may be controlled by a series of commands received from the processor 20. Alternatively, the processor 20 may control the camera 12 or the orienting mechanism 16 by means of a manually controlled input device 23 such as a keyboard, mouse, joystick, other similar peripheral, or any combination thereof.

Thus, the orienting mechanism 16 of the local positioning system instrument 17 may be controlled by the processor 20 to position the field of view 24 of the camera 12 at various locations on the target object 18. For example, as shown in FIG. 1, the orienting mechanism 16 may pan the field of view 26 horizontally along the target object 18 as the target object incrementally rotates in the direction shown by arrow 22. Therefore, the entire surface 19 of the target object 18 may be imaged by the camera 12.

The memory 54 may contain a three-dimensional (3D) localization software program. The 3D localization software may use one or more calibration points 27 at a distance on the surface 19 of the target object 18 to determine an initial position and orientation of the local positioning system instrument 17 relative to the target object 18. In order to obtain the highest accuracy for calibration, the calibration points 27 may be spread out over the extents of the surface 19 of the target object 18. Alternatively, the calibration points 27 may be located somewhere other than on the target object 18, such as on the support structure 35 that supports the target object 18.

The 3D localization software may utilize the calibration points 27 in combination with orientation data (e.g., pan and tilt data) obtained by way of communication with the orienting mechanism 16 and distance data (e.g., the distance from the local positioning system instrument 17 to the calibration points 27) obtained by way of communication with the laser emitting device 14 to define the relative position and orientation of the local positioning system instrument 17 with respect to the target object 18. The calibration points 27 may be visible features of known position in the local coordinate system 46 of the target object 18 as determined from a 3D CAD model or other measurement technique. The calibration points 27 may be used in coordination with the orientation data (e.g., azimuth and elevation angles) from the orienting mechanism 16 and distance data from the laser emitting device 14 (laser range meter) to solve for the camera position and orientation relative to the target object 18.

The use of a local positioning system to determine the location of a point of interest on a target object relative to the coordinate system of the target object is described in greater detail in U.S. Pat. No. 7,859,655 to Troy et al. issued on Dec. 28, 2010 and U.S. Pat. No. 8,044,991 to Lea et al. issued on Oct. 25, 2011. The entire contents of both U.S. Pat. Nos. 7,859,655 and 8,044,991 are incorporated herein by reference.

Once the position and orientation of the camera 12 with respect to the target object 18 are determined, the processor 20 may direct the camera 12 to begin collecting images of the target object 18. For each image captured, the orientation of the camera 12 (which may include the angle of the camera 12 along the azimuth axis 50 and the elevation axis 52) may be recorded to the memory 54. By using the azimuth and elevation angles from the orienting mechanism 16 and the relative position and orientation of the camera 12 determined in the calibration process, the location of each image can be determined relative to the coordinate system 46 of the target object 18.

For each image captured by the camera 12, the processor 20 may retrieve a reference image from the memory 54 and may utilize the image processing functionality to compare the reference image to the captured image. If the processor 20 determines that sufficient differences exist between the captured image and the reference image, the processor 20 may conclude that a discrepancy 26 is present within the captured image. The processor 20 may then store in memory 54 the location of the discrepancy 26 relative to the coordinate system 46 of the target object 18.

At this point, those skilled in the art will appreciate that the processor 20 may determine the location (relative to the coordinate system 46 of the target object 18) of each image captured by the camera 12 with respect to a reference point (e.g., the center point) within the captured image. When a discrepancy 26 is found within the captured image, the processor 20 may determine the location (relative to the coordinate system 46 of the target object 18) of the discrepancy 26 by determining the location of the discrepancy 26 relative to the known location of the reference point.

The use of a local positioning system along with image processing to detect and determine the location of discrepancies on a target object relative to the coordinate system of the target object is described in greater detail in U.S. Ser. No. 12/897,408 submitted the United States Patent and Trademark Office on Oct. 4, 2010, the entire contents of which are incorporated herein by reference.

The process of (1) tracking the position/orientation of the target object, (2) collecting images of the target object 18, (3) analyzing the captured images to detect discrepancies 26 on the target object 18, and (4) determining the location of the discrepancies 26 relative to the coordinate system 46 of the target object 18 may be repeated until the entire target object 18 has been imaged and all discrepancies detected.

The laser emitting device 14 may be mounted to the camera 12 so that it points in the same direction as the camera lens 13 and has a direction vector 34 that is similar to the direction vector 32 of the camera 12. The processor 20 may calculate the differences in vectors 34, 32 by measuring the relative locations of the camera 12 and the laser emitting device 14.

Alternatively, the laser emitting device 14 may be mounted to the camera 12 so that it has a direction vector 34 that is substantially identical to the direction vector 32 of the camera. In this instance, the camera and the laser emitting device 14 have the same optical path, and no calculation of the differences in vectors 32, 34 may be necessary.

At a time when it is necessary to locate the points of interest 30 stored in the memory 54 as known discrepancies 26, the processor 20 may retrieve the coordinates from the memory 54. Similar to the process described above for orienting the camera 12 with respect to the target object 18 and locating the point of interest 30, the processor 20 may direct the orienting mechanism 16 to rotate or aim the laser emitting device 14 upon the stored location of the point of interest 30 (i.e., the discrepancy 26). At this position, the orientation of the laser emitting device 14 (which may include the angle of the laser emitting device 14 along the azimuth axis 50 and the elevation axis 52) may be adjusted to move to the coordinates stored in the memory 54. By using the azimuth and elevation angles from the orienting mechanism 16 and the relative position and orientation of the laser emitting device 14 determined in the calibration process, the laser emitting device 14 may be positioned so that it is aimed directly at the point of interest 30 on the surface 19 of the target object 18.

When the target object 18 has rotated about axis A, the processor 20 may also obtain position/orientation data from the tracking unit 37 to further calculate the coordinates of the point of interest 30.

Once properly aimed at the point of interest, the laser emitting device 14 may be directed by the processor 20 to emit a laser beam. The laser beam may be any type of laser that is suitable for marking or otherwise "pointing out" a point of interest 30 in such a way that is visible to the human eye, either aided or unaided with an optical apparatus.

In an alternate implementation, the detection system may be integrated into an application connected to the internet, such as a Web-enabled application, which may be either wired or wireless. In this type of application, remote users, or other automated software agents, may operate the camera 12, the laser emitting device 14, or the orienting mechanism 16, and then receive the processed localization data for objects within visual range of the system. Remote users may then also direct the laser emitting device 14 to indicate the discrepancies 26 discovered by the camera 12.

Figure 2:
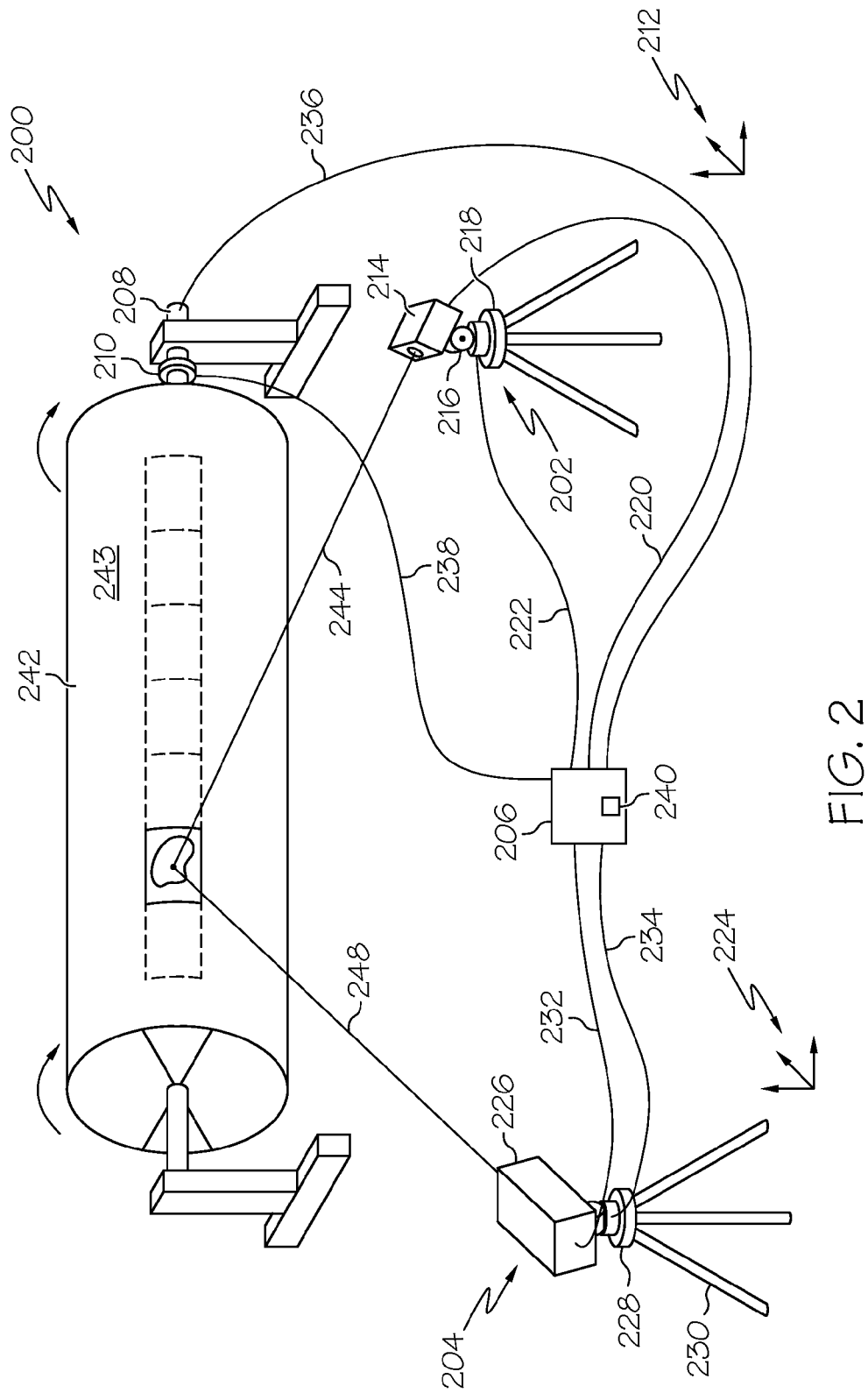
FIG. 2 is a schematic perspective view of another embodiment of the disclosed detection system.

Referring to FIG. 2, a second embodiment of the disclosed local positioning-based automated detection system, generally designated 200, may include a first local positioning system instrument 202, a second local positioning system instrument 204, a processor 206, a tracking unit 208 and a controllable motion actuator 210. Therefore, in detection system 200, the first local positioning system instrument 202 may be operated independently of the second local positioning system instrument 204, but both instruments 202, 204 may be calibrated to the same target object 242.

The first local positioning system instrument 202 may have a coordinate system 212, and may include a camera and a laser emitting device (shown collectively as 214), an orienting mechanism 216 and a support structure 218. The camera and laser emitting devices 214 may be in communication with the processor 206 by way of pathway 220 and the orienting mechanism 216 may be in communication with the processor 206 by way of pathway 222.

The second local positioning system instrument 204 may have a coordinate system 224, and may include a camera and a laser emitting device (shown collectively as 226), an orienting mechanism 228 and a support structure 230. The camera and laser emitting devices 226 may be in communication with the processor 206 by way of pathway 232 and the orienting mechanism 228 may be in communication with the processor 206 by way of pathway 234.

The processor 206 may additionally be in communication with the tracking unit 208 by way of pathway 236 and the controllable motion actuator 210 by way of pathway 238. The processor 206 may also have access to memory 240.

Accordingly, the position and orientation of the first local positioning system instrument 202 relative to the target object 242 must be known and calculated by the processor 206 and stored in memory 240, and the position and orientation of the second local positioning system instrument 204 relative to the target object 242 must be known and calculated by the processor 206 and stored in memory 240

When the two local positioning system instruments 202, 204 are calibrated to the same target object 242, the position pointed to by each instrument 202, 204 is the same point and the laser beams 244, 248 intersect on the surface 243 of the target object 242. Other than the different locations of the two instruments 202, 204, all other aspects may remain as described above.

Accordingly, such a multi-system configuration may provide additional coverage of larger target objects, and may also be used to provide redundancy in situations where the beam from one system is occluded.

Figure 3:
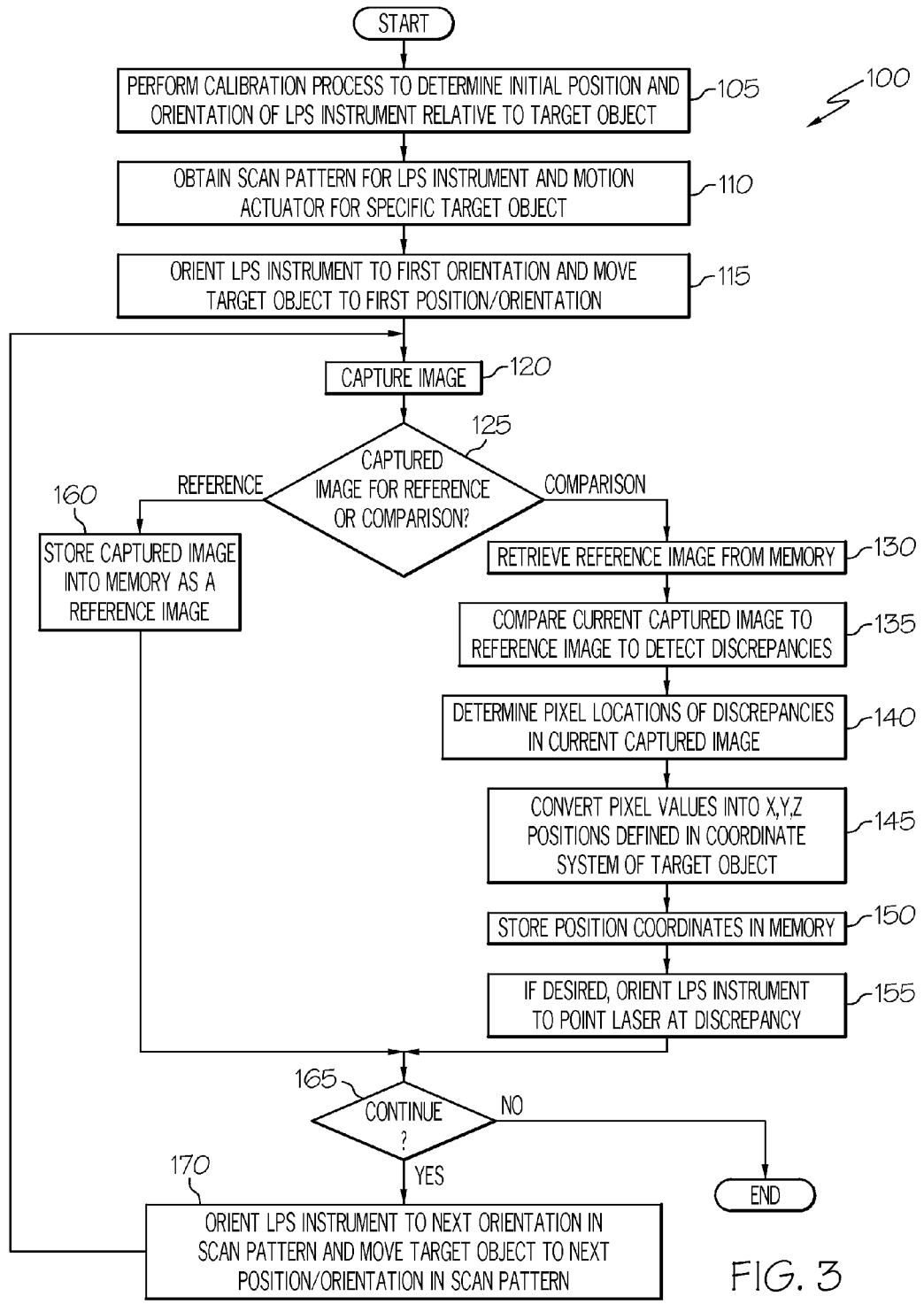
FIG. 3 is a flow chart of one embodiment of the disclosed detection method

Referring to FIG. 3, also disclosed is a method, generally designated 100, for detecting and indicating a discrepancy on a target object. The method 100 may employ a local positioning system instrument having a camera and a laser emitting device, as well as a motion actuator, a tracking unit and image processing functionality to detect discrepancies on the target object. Additionally, the method 100 may employ three-dimensional localization software to determine the location of the detected discrepancies relative to the coordinate system of the target object.

The method 100 may begin at block 105 with the step of performing a calibration process. The position and orientation of the local positioning system instrument relative to the target object may be determined using various calibration techniques, such as detecting calibration points or using a laser to measure distance to a known location on the target object. Other calibration techniques are also contemplated.

At block 110, data may be obtained by the image processing functionality. Data may include a scan pattern for the camera and the motion actuator data for the target object. The camera may be oriented such that the camera's field of view is on a portion of the target object, and the motion actuator may move the target object into an initial orientation, as shown at block 115.

At block 120, an image of a portion of the target object may be captured by the camera. At block 125, a determination may be made whether the captured image is a reference image or a comparison image. If the image is a reference image, then, as shown at block 160, the image may be stored to memory for future use.

If the captured image from block 120 is a comparison image, then a reference image may be retrieved from memory (block 130), and the two images may be compared to detect discrepancies (block 135). When discrepancies are detected, a determination may be made as to the pixel locations of the discrepancies in the comparison image, as shown at block 140.

At block 145, the location of the discrepancy may be determined relative to the coordinate system of the target object. The step of determining the location of the discrepancy relative to the coordinate system of the target object may employ three-dimensional localization software, which may convert the pixel values into three dimensional coordinates.

At block 150, the location of the discrepancy relative to the coordinate system of the target object may be stored in memory. The location of the discrepancy may be stored in memory as coordinate data.

Thus, when desired, a laser emitting device may be actuated to point a laser beam at the discrepancy. The laser emitting device may be oriented relative to the target object to project the laser beam at the discrepancy based on the coordinate data stored in memory, as in block 155.

If further action is necessary, as in block 165, the camera may be pointed to another location on the target object and, if necessary, the motion actuator may be directed to move the target object to a new position, as in block 170. The process may then repeat by obtaining a new image, as in block 120.

Accordingly, the disclosed detection system and method provide an easy and accurate way to detect discrepancies on a target object and then, when desired, point-out the discrepancies such that measures may be taken to address (e.g., repair or remove) the discrepancies.

Although various aspects of the disclosed local positioning-based automated detection system have been shown and described, modifications may occur to those skilled in the art upon reading the specification. The present application includes such modifications and is limited only by the scope of the claims.

What is claimed is:
1. A detection system comprising:
a target object having a target object coordinate system;
a tracking unit configured to monitor at least one of a position and an orientation of said target object and generate a target object position signal indicative of said at least one of said position and said orientation of said target object, wherein said target object is movable to a first target object position or orientation and a second target object position or orientation;
a camera configured to scan said target object and capture images of said target object;

an orienting mechanism connected to said camera to control an orientation of said camera relative to said target object; and a processor configured to automatically:
adjust said orientation of said camera relative to said target object to scan, with said camera, one or more locations on said target object at said first target object position or orientation and said second target object position or orientation;
capture first images of first locations and second images of second locations on said target object at said first target object position or orientation and said second target object position or orientation, respectively;
select and retrieve first reference images of said target object associated with said first locations on said target object at said first target object position or orientation and second reference images of said target object associated with said second locations on said target object at said second target object position or orientation;
analyze each first image of said first images by comparing said first image to a corresponding first reference image of said first reference images and each second image of said second images by comparing said second image to a corresponding second reference image of said second reference images;
detect the presence, if any, of a first discrepancy in said first image as compared to said corresponding first reference image and a second discrepancy is said second image as compared to said corresponding second reference image; and
determine, when detected, a three-dimensional location of said first discrepancy and said second discrepancy relative to said target object coordinate system based at least upon said target object position signal at said first target object position or orientation and said second target object position or orientation, respectively, a position and said orientation of said camera, a pixel location of said first discrepancy in said first image, and a pixel location of said second discrepancy in said second image.

2. The detection system of claim 1 wherein said target object is mounted on a support structure and rotates relative to said support structure about an axis of rotation.

3. The detection system of claim 2 wherein said tracking unit comprises an encoder.

4. The detection system of claim 1 wherein said orienting mechanism is controllable by said processor.

5. The detection system of claim 1 wherein said orienting mechanism comprises a pan-tilt mechanism.

6. The detection system of claim 1 further comprising a memory, wherein said processor stores in said memory said location of said discrepancy as coordinate data.

7. The detection system of claim 6 wherein said reference images are stored in said memory.

8. The detection system of claim 1 further comprising a laser emitting device positioned to project a laser beam onto said target object.

9. The detection system of claim 8 wherein said laser emitting device is connected to said orienting mechanism such that said orienting mechanism controls an orientation of said laser emitting device relative to said target object.

10. The detection system of claim 9 wherein said orientation of said laser emitting device is controllable by said processor to project said laser beam onto said target object identifying a location of said discrepancy, when said discrepancy is detected.

11. The detection system of claim 8 wherein said laser emitting device is configured as a laser range meter.

12. The detection system of claim 1 further comprising a motion actuator coupled to said target object, said motion actuator being controllable by said processor to control at least one of said position and said orientation of said target object.

13. The detection system of claim 12 wherein said motion actuator comprises an electric motor.

14. A detection system comprising:
a target object having a target object coordinate system;
a motion actuator coupled to said target object to control at least one of a position and an orientation of said target object, wherein said target object is movable to a first target object position or orientation and a second target object position or orientation;
a tracking unit configured to monitor said at least one of said position and said orientation of said target object and generate a target object position signal indicative of said at least one of said position and said orientation of said target object;
a local positioning system instrument positioned relative to said target object, said local positioning system instrument comprising:
a camera configured to scan said target object and capture images of said target object; and
an orienting mechanism connected to said camera to control an orientation of said camera; and
a processor configured to automatically:
adjust said orientation of said camera relative to said target object to scan one or more portions of said target object with said camera, when said target object is moved to said first target object position or orientation;
capture said images at different locations on said target object;
select and retrieve reference images of said target object associated with said different locations on said target object;
analyze each image of said images by comparing said image to a corresponding reference image of said reference images;
detect the presence, if any, of a discrepancy in said image as compared to said corresponding reference image;
determine a three-dimensional location of said discrepancy relative to said target object coordinate system based at least upon said target object position signal at said first target object position or orientation, said orientation of said camera, and a pixel location of said discrepancy in said image, when said discrepancy is detected in said image;
adjust said orientation of said camera relative to said target object to scan one or more portions of said target object with said camera, when said target object is moved to said second target object position or orientation;
capture additional images at additional different locations on said target object;
select and retrieve additional reference images of said target object associated with said additional different locations on said target object;
analyze each additional image of said additional images by comparing said additional image to a corresponding additional reference image of said additional reference images;

detect the presence, if any, of an additional discrepancy in said additional image as compared to said corresponding additional reference image;

determine a three-dimensional location of said additional discrepancy relative to said target object coordinate system based at least upon said target object position signal at said second target object position or orientation, said orientation of said camera, and a pixel location of said discrepancy in said image, when said additional discrepancy is detected in said additional image.

15. A method for detecting a discrepancy on a target object, said target object having a target object coordinate system, said method comprising the steps of:

providing a local positioning system instrument comprising a camera, and an orienting mechanism for controlling an orientation of said camera relative to said target object;

providing a motion actuator configured to selectively move said target object;

providing a tracking unit configured to monitor at least one of a position and an orientation of said target object;

determining at least one of an initial position and an initial orientation of said local positioning system instrument relative to said target object;

moving said target object to a first target object position or orientation;

automatically adjusting said orientation of said camera relative to said target object at said first target object position or orientation to scan one or more portions of said target object with said camera;

automatically capturing images of said target object at different locations on said target object;

automatically selecting and retrieving reference images of said target object associated with said different locations on said target object;

automatically comparing each image of said images to a corresponding reference image of said reference images;

automatically detecting the presence, if any, of a discrepancy in said image as compared to said reference image; and automatically determining three-dimensional coordinates of said discrepancy in said target object coordinate system based at least upon said first target object position or orientation, said orientation of said camera corresponding to said image having said discrepancy, and a pixel location of said discrepancy in said image, when said discrepancy is present in said image;

moving said target object to a second target object position or orientation;

automatically adjusting said orientation of said camera relative to said target object at said second target object position or orientation to scan at least a portion of said target object with said camera;

automatically capturing additional images of said target object at additional different locations on said target object;

automatically selecting and retrieving additional reference images of said target object associated with said additional different locations on said target object;

automatically comparing each additional image of said additional images to a corresponding additional reference image of said additional reference images;

automatically detecting the presence, if any, of an additional discrepancy in said additional image as compared to said additional reference image; and automatically determining three-dimensional coordinates of said additional discrepancy in said target object coordinate system based at least upon said second target object position or orientation, said orientation of said camera corresponding to said additional image having said additional discrepancy, and a pixel location of said additional discrepancy in said additional image, when said additional discrepancy is present in said additional image.

16. The method of claim 15 wherein said step of determining said three-dimensional coordinates comprises the steps of:

determining pixel locations of said discrepancy; and
converting said pixel locations into said three-dimensional coordinates.

17. The method of claim 15 further comprising the step of storing said three-dimensional coordinates in memory.

18. The method of claim 15 wherein said local positioning system instrument further comprises a laser emitting device, wherein said orienting mechanism controls an orientation of said laser emitting device relative to said target object, and further comprising the step of orienting said laser emitting device relative to said target object to project a laser beam onto said target object identifying a location of said discrepancy.

19. The method of claim 15 further comprising the step of activating an alarm when said discrepancy is present in said image.

20. The detection system of claim 14 wherein said local positioning system instrument further comprises a laser emitting device configured to project a laser beam onto said target object and determine a distance between said target object and said local positioning system instrument, and wherein said processor is further configured to project said laser beam onto said discrepancy by controlling said orientation of said laser emitting device based on said location of said discrepancy relative to said target object coordinate system.

* * * * *